(12) United States Patent
Sondermeijer et al.

(10) Patent No.: US 6,521,236 B1
(45) Date of Patent: Feb. 18, 2003

(54) VECTOR VACCINE OF RECOMBINANT FELINE HERPESVIRUS

(75) Inventors: Paulus Jacobus Antonius Sondermeijer, Boxmeer; Martha Jacoba Willemse, Nijmegen, both of (NL)

(73) Assignee: Akzo Nobel N.V., Arnhem (NL)

(*) Notice: Subject to any disclaimer, the term of this patent is extended or adjusted under 35 U.S.C. 154(b) by 0 days.

(21) Appl. No.: 08/504,617

(22) Filed: Jul. 20, 1995

Related U.S. Application Data

(63) Continuation of application No. 08/211,150, filed as application No. PCT/EP93/01971 on Jul. 23, 1993, now abandoned.

(30) Foreign Application Priority Data

Jul. 30, 1992 (EP) .............................................. 92202365

(51) Int. Cl.[7] ...................... A61K 39/245; A61K 39/12; C12P 21/06; C12N 15/63

(52) U.S. Cl. ................................ 424/229.1; 424/184.1; 424/199.1; 435/235.1; 435/455; 435/320.1; 435/69.1; 435/252.3; 435/325; 435/236; 536/23.1; 536/23.72

(58) Field of Search ............................. 435/235.1, 320.1, 435/252.3, 69.1, 455, 325; 424/199.1, 229.1, 184.1, 185.1, 187.1, 205.1, 207.1, 208.1; 536/23.1, 23.72

(56) References Cited

U.S. PATENT DOCUMENTS

| | | | | |
|---|---|---|---|---|
| 4,810,634 A | * | 3/1989 | Post et al. ................ | 435/235.1 |
| 5,223,424 A | * | 6/1993 | Cochran et al. ............ | 435/236 |
| 5,324,664 A | * | 6/1994 | Nunberg et al. .......... | 435/320.1 |

FOREIGN PATENT DOCUMENTS

| | | |
|---|---|---|
| EP | 0431668 | 6/1991 |
| EP | 0477056 | 9/1991 |
| WO | WO 95/00172 | 1/1995 |

OTHER PUBLICATIONS

Horimoto, T. Et Al. 1992. Arch. Virol vol. 126 p. 283–292.*
Kimman, T. G. Et Al. 1992. J. Gen. Virol. vol. 73 p. 243–251.*
Longnecker, R. Et Al. 1987. Science vol. 236 p. 573–576.*
Weber, P.C. Et Al. 1987. Science vol. 236 p. 576–579.*
Cantello, J.L. Et Al. 1981. J. Virol. vol. 65 p. 1584–1588.*
Spatz, S.J. Et Al. 1994. J. Gen. Virol. vol. 75 p. 1235–1244.*
Flowers, C.C. Et Al. 1992. Virol. vol. 190 p. 307–315.*
Ross, L.J.N. Et Al. 1991. J. Gen. Virol. vol. 72 p. 939–947.*
Lerner et al. "The Development of Synthetic Vaccines". Biology of Immunologic Diseases. Dixon, Eds. pp. 331–338.*
Burgener, D.C. "Glycoprotein–specific immune responses in cats after exposure to feline herpesvirus–1". A,erican Journal of Veterinary Research. vol. 49, No 10:1673–1676, 1998.*

(List continued on next page.)

Primary Examiner—Hankyel T. Park
Assistant Examiner—Stacy S. Brown
(74) Attorney, Agent, or Firm—Mark W. Milstead; William M. Blackstone

(57) ABSTRACT

The present invention is concerned with a Feline Herpesvirus (FHV) mutant comprising a heterologous gene or foreign DNA inserted into a section of the FHV genome. The invention also relates to a vector vaccine comprising a recombinant FHV mutant which expresses a heterologous polypeptide derived from a feline pathogen and a pharmaceutically acceptable carrier and induces an immune response in an inoculated host against both FHV and the feline pathogen.

29 Claims, 6 Drawing Sheets

OTHER PUBLICATIONS

Quint et al. "Construction and Characterization od Deletion Mutants of Pseudorabies Virus: a New Generation of 'Live Vaccines". Journal General Virology. vol. 68:523–534, 1987.*

Zijl et al. "Identication of two genes in the unique short region of pseudorabies virus: comparison with herpes simplex virus and varicella–zoster virus". Journal General Virology. vol. 71:1747–1755, 1990.*

Spatz et al. "Identification of feline herpesvirus type 1 (FHV–1) genes encoding glycoproteins G, D, I and E: expression of FHV–1 glycoprotein D in vaccinia and racoon poxviruses". Journal General Virology. vol. 75:1235–1244, 1994.*

J.C. Audonnet et al., "Equine herpesvirus type 1 unique short fragment encodes glycoproteins with homology to herpes simplex virus type 1 gD, gI and gE," Journal of General Virology, vol. 71, pp 2696–2978, Great Britian, 1990.

A. Grail et al., "Restriction endonuclease mapping of the genome of feline herpesvirus type 1," Archives of Virology, vol. 116, Nos. 1–4, p. 209–220, 1991.

PA Rota et al., "Physical characterization of the genome of feline herpesvirus–1" Virology, vol. 154, No. 1, 1986, p. 168–179, USA.

* cited by examiner-

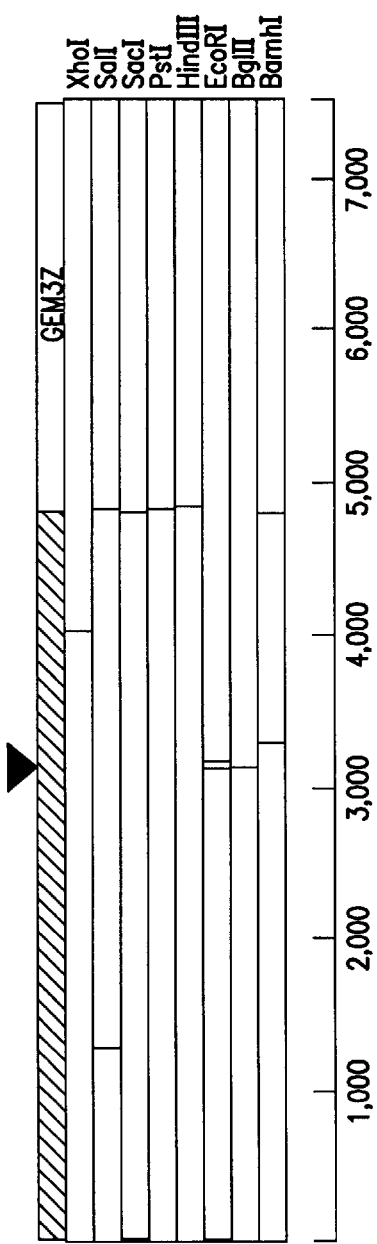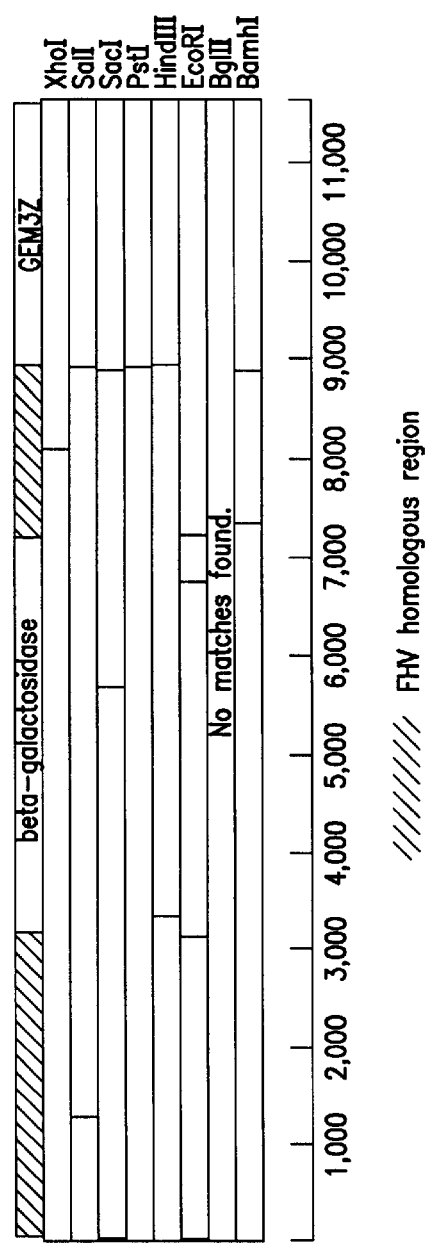
FIG. 2A
FIG. 2B

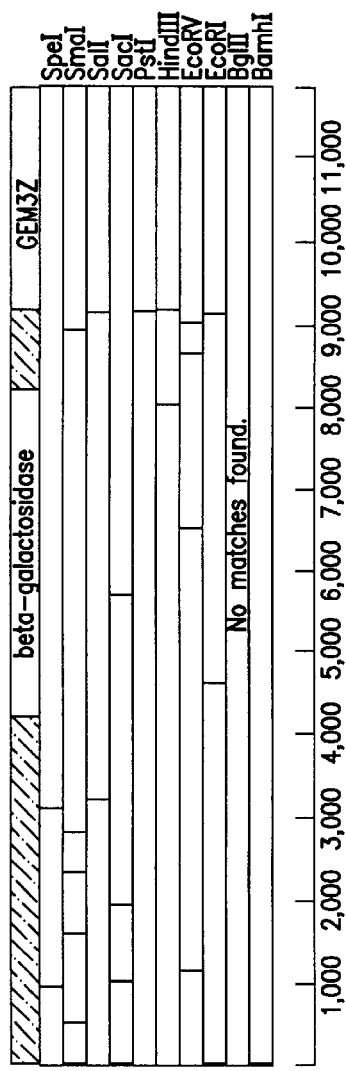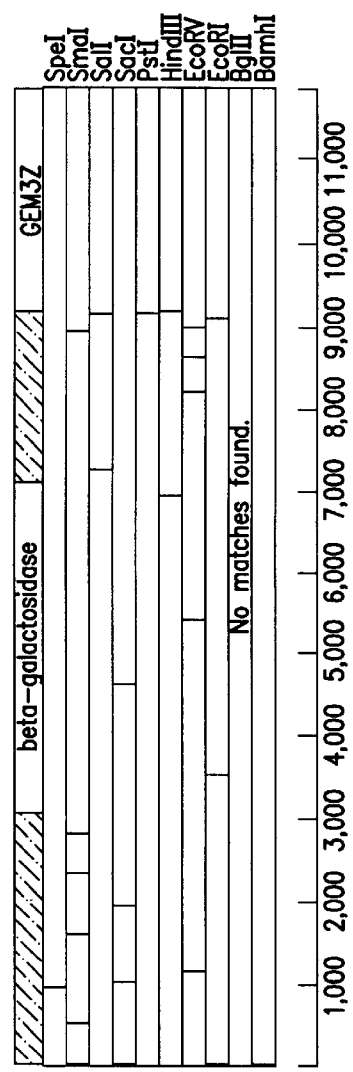
FIG. 5A
FIG. 5B
▨ FHV homologous region

VECTOR VACCINE OF RECOMBINANT FELINE HERPESVIRUS

This is a continuation of U.S. Ser. No. 08/211,150, filed Mar. 22, 1994, now abandoned, which is a National Phase Application of PCT/EP93/01971, filed Jul. 23, 1993.

FIELD OF THE INVENTION

The present invention is concerned with a feline herpesvirus (FHV) mutant comprising a mutation in a section of the FHV genome, a nucleic acid sequence comprising said section of the FHV genome, a nucleic acid sequence comprising a heterologous DNA sequence flanked by DNA derived from said section, a recombinant DNA molecule comprising such nucleic acid sequences, a cell culture infected with an FHV mutant, as well as vaccine comprising the FHV mutant.

One of the major clinical problems in diseases of Felidae is associated with respiratory tract infections. The great majority of these cases are caused by either feline herpesvirus 1 (FHV) or feline calicivirus.

BACKGROUND OF THE INVENTION

FHV is the causative agent of feline viral rhinotracheitis in cats. In kittens, FHV infection can generalize resulting in mortality rates of up to 50%. The disease is common and is found world-wide and is characterized by sneezing, depression, and ocular and nasal discharge.

The FHV is a member of the family Herpes-viridae, subfamily A,-herpesvirus. The genome is about 126 kb in length and is composed of a unique long ($U_L$) region of about 99 kb and a short region of 27 kb comprising an unique short ($U_s$) region of about 9 kb flanked by inverted repeats of about 8 kb (Grail et al., Arch. Virol. 116, 209–220, 1991).

Because of the prevalence and seriousness of FHV infection, feline viral rhinotracheitis vaccines comprising modified live or killed FHV have been developed and have resulted in a successful reduction of the incidence of the disease.

In addition to FHV infection, cats are also susceptible to infection by various other pathogens, such as feline leukemia virus, feline calicivirus, feline immunodeficiency virus, feline coronavirus and feline Chlamydia.

At present, in general, cats can be protected against infection by these pathogenic micro-organisms with live or inactivated vaccines.

However, these types of vaccines may suffer from a number of drawbacks. Using attenuated live vaccines always involves the risk of inoculating animals with inadequately attenuated pathogenic micro-organisms. In addition, the attenuated pathogens may revert to a virulent state resulting in disease of the inoculated animals and the possible spread of the pathogen to other animals.

Inactivated vaccines generally induce only a low level of immunity, requiring repeated immunizations. Furthermore, the neutralization inducing antigenic determinants of the pathogens may become altered by the inactivation treatment, decreasing the protective potency of the vaccine.

Moreover, a problem with combined live viral vaccines is the mutual influence of the antigenic components resulting in a decrease of the potency of one or more of the constituting components.

Furthermore, with currently administered live attenuated or inactivated FHV vaccines it is not possible to determine whether a specific animal is a carrier of an FHV field virus or whether the animal was vaccinated. Hence, it is important to discriminate between animals vaccinated with an FHV vaccine and those infected with a field virus so as to be able to take appropriate measures to reduce spreading of a virulent field virus. The introduction of for example a serologically identifiable marker can be achieved by introducing a mutation in genes encoding non-essential (glyco) proteins of the FHV which normally give rise to the production of antibodies in an infected host animal.

SUMMARY OF THE INVENTION

It is an object of the present invention to provide an FHV mutant which can be used not only for the preparation of a vaccine against feline viral rhinotracheitis but also against other infectious diseases of Felidae, which obviates any potential risk associated with the use of a live attenuated pathogen as a vaccine, which stimulates both the humoral and cellular immune system in a potent way without the explicit need of an adjuvant and which offers the possibility of a multivalent vaccine without the risk of adverse mutual interference of different antigenic components.

An other object of the present invention is to provide an FHV vaccine virus which is distinguishable from any field strain or any other FHV vaccine virus.

Restriction map of the 13.5 kb DNA insert from λFHV04. The positian of this DNA fragment is mapped in the rightward part of the unique short region of the FHV genome. The insertion region is composed of the six open reading frames indicated at the top including intergenic non-translated sequences. The subcloning of the 4.8 kb SacI and 5.2 kb BamHI restriction fragments in pGEM3Z resulted in pFHV13 and pFHV10, respectively. The sequence analysis indicated that the most left-ward EcoRI restriction site contained two six-base recognition sequences which were located within 50 bp from each other.

FIG. 2

A Restriction map of plasmid pFHV13, a derivative of pGEM3Z containing the 4.8 kb SacI from λFHV04. The unique BglII at 3.1 kb, which was used for inserting DNA, is labelled with a triangle.

B Restriction map of plasmid pFHV19, derived from pFHV13 by insertion of a 4.0 kb BamHI fragment containing the β-galactosidaoe marker gene.

FIG. 3

A Restriction map of plasmid pFHV10, a derivative of pGEM3Z containing the 5.2 kb BamHI fragment from λFHV04. The Sau3A site labelled with a triangle was used for the insertion of DNA.

B Restriction map of plasmid pFHV23, derived from pFHV10 by insertion of a 4.0 kb BamHI fragment containing the β-galactosidase marker gene.

FIG. 4

Detailed restriction map derived from the sequence listed in SEQ ID No:1. Positions of the six open reading frames are indicated in the top. The EcoRV site at 2.1 kb was used for insertion of marker gene into ORF-2 by contransfections of viral DNA with the plasmid pFHV60.

The Spe I site at 3.1 kw was used in a similar manner to insert the marker gene into ORF-3. In this case, plasmid pFHV55 was used in the contransfections.

FIG. 5

Restriction map of pFHV60 (A) and pFHV55 (B) which were both derived from pFHV40. This plasmid was derived from pFHV10 by deletion of a 0.2 kb Bam HI-BglII fragment around 5.1 kb (FIG. 3A), such that both restriction sites were not restored after ligation.

Figure 4:
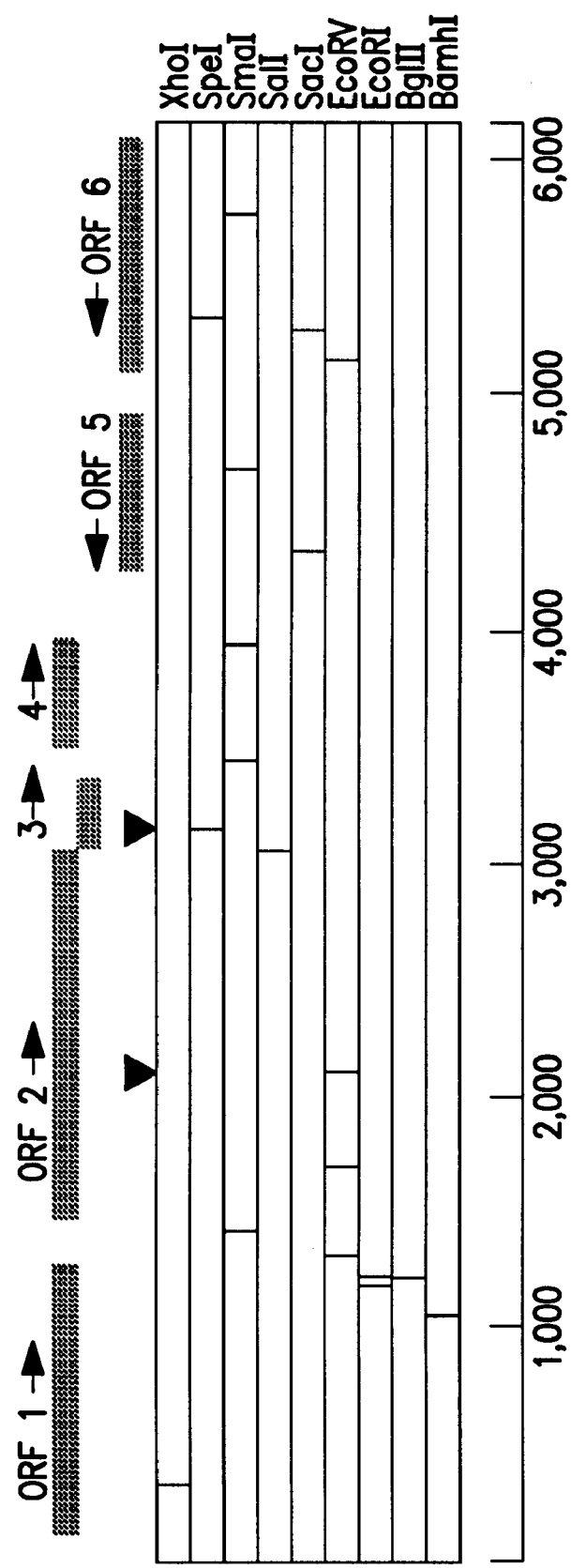

A. Restriction map of pFHV60, a derivative of pFHV40 with an insertion of the β-galactosidase gene at a position equivalent to the EcoRV site which is indicated in FIG. 4. This insertion disrupts the coding sequence of ORF-2.

B. Restriction map of pFHV55, derived from pFHV40 by insertion at the Spe I site shown in FIG. 4. The coding sequence of ORF-3 is disrupted in this construct.

FIG. 6

Restriction map of pFHV38. The in vivo, recombination vector contains the LTR promotor necessary for the expression of foreign genes which can be inserted downstream of the promotor at the restriction site e.g. BglII or SalI.

DETAILED DESCRIPTION OF THE INVENTION

Figure 1:
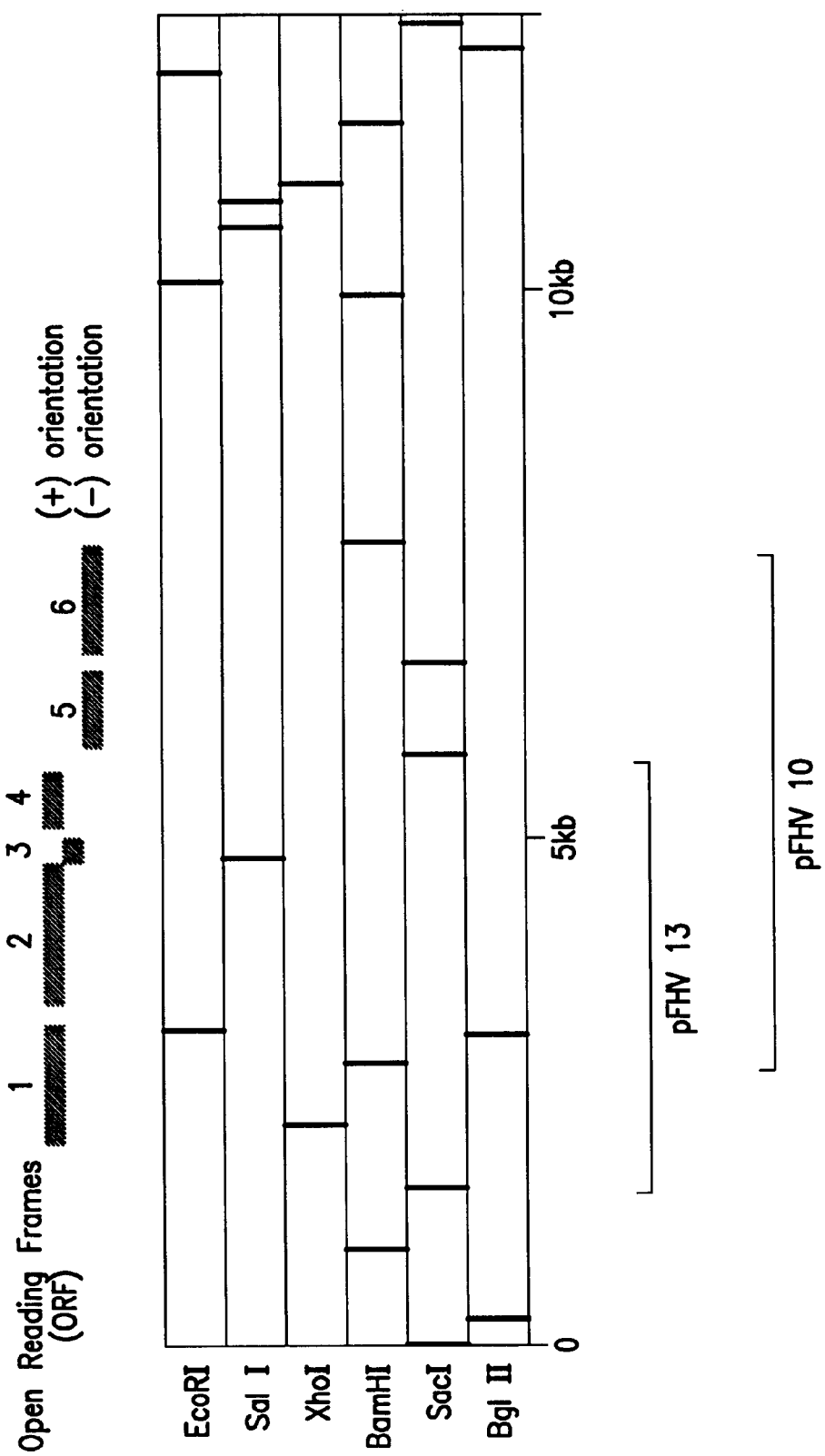
FIG. 1

The present invention provides an FHV mutant comprising a mutation in a section of an FHV genome which spans from the upstream non-coding region of open reading frame-1 up to and including the downstream non-coding region of open reading frame-6 localized within a DNA fragment of the FHV genome having a restriction enzyme map essentially defined by FIG. 1.

A mutation is understood to be a change of the genetic information in the above-mentioned section with respect to the genetic information present in this section of the genome of the parent FHV.

The mutation is in particular, a nucleic acid substitution, deletion, insertion or inversion, or a combination thereof resulting in a FHV mutant which fails to produce one or more antigenic or functional polypeptides shown in SEQ ID NO: 2–7, or in an FHV mutant which contains an inserted heterologous nucleic acid sequence.

The FHV mutant according to the present invention can be derived from any FHV strain, e.g. strain G2620 (commercially available from Intervet International B.V., the Netherlands), C-27 (ATCC VR-636), FVRm (ATCC VR-814), FVRM vaccine (ATCC VR-815) or F2.

The term "polypeptide" as used herein refers to a molecular chain of amino acids, does not refer to a specific length of the product and if required can be modified in vivo or in vitro, for example by glycosylation, amidation, carboxylation or phosphorylation; thus inter alia peptides, oligopeptides and proteins are included within the definition of polypeptide.

The prerequisite for a useful FHV mutant according to the present invention is that the mutation is introduced in a permissive position or region of the genomic FHV sequence, i.e. a position or region which can be used for the incorporation of the mutation without disrupting essential functions of FHV such as those necessary for infection or replication.

Until now little is known about the localization of genes in the FHV genome. Rota et al. (Virology 154, 168–179, 1986) and Grail et al. (Arch. Virol. 116, 209–220, 1991) disclosed physical maps of the FHV genome.

Nunberg et al. (J. Virology 63, 3240–3249, 1989) and Cole et al. (J. Virology 64, 4930–4938, 1990) identified the thymidine kinase (TK) gene and mapped this gene in the SalI-A restriction fragment (Rota et al., supra) of the FHV genome. Subsequently, several recombinant FHV strains were constructed in which FeLV env and gag genes have been inserted within the FHV TK gene.

The section of the FHV genome referred to in the present invention has not been identified previously within the FHV genome. Surprisingly, it has been found that a mutation such as the incorporation of heterologous DNA is allowable in this region without disrupting essential functions of the FHV.

The section of the FHV genome used to introduce one or more mutations in order to prepare a FHV mutant according to the invention is located within a 13.5 kb restriction fragment generated by partial digestion of genomic FHV DNA with the enzyme Sau3A (FIG. 1).

Said fragment is analyzed in detail by restriction enzyme mapping and essentially corresponds to a region within the Us segment of the viral genome between map unit 0.87 and 0.96 on the map of Grail et al. (supra).

The section of the FHV genome used in the present invention for the introduction of one or more mutations is located within two adjacent BamHI fragments of 1.9 and 5.2 kb, is about 6.1 kb in length and comprises the DNA sequence of six consecutive open reading frames (ORF) as well as the intergenic sequences flanking these open reading frames, including the upstream non-coding sequence of ORF-1 and the downstream non-coding sequence of ORF-6.

These flanking intergenic sequences do not form part of an ORF or protein encoding DNA sequence, or do not comprise sequences regulating the replication of the virus. Said flanking sequences extend in the upstream and downstream direction up to the start or end of the nearest open reading frame.

In particular, the present invention provides an FHV mutant containing a mutation in a section of the FHV genome which spans the region comprising the DNA sequence of ORF 1–6 encoding polypeptides shown in SEQ ID NO: 2–7 and intergenic flanking sequences thereof, and more preferably the region comprising the DNA sequence shown in SEQ ID NO: 1.

ORF-1 is an open reading frame located between nucleotide positions 127 and 1281 (SEQ ID NO: 1) and encodes a polypeptide of 384 amino acids (SEQ ID NO: 2) and contains the unique BglII site at nucleotide position 1210 used for the insertion of the β-galactosidase marker gene, thereby indicating that the hypothetical polypeptide encoded by ORF-1 does not have essential functions for the infection of cells or replication of the virus.

ORF-2 starts at nucleotide position 1460 and continues up to nucleotide position 3058 (SEQ ID NO: 1) encoding a polypeptide of 532 amino acids (SEQ ID NO: 3). The β-galactosidase marker gene was also inserted into one of the EcoRV sites of this ORF.

ORF-3 is a small open reading frame and is identified in another phase than ORF-2 and shares a common nucleotide-sequence with ORF-2. ORF-3 is located between nucleotide position 3055 and 3357 (SEQ ID NO: 1) and encodes a polypeptide of 100 amino acids (SEQ ID NO: 4). The Spe I site was selected for the insertion of the β-galactosidase marker gene.

ORF-4 starts at nucleotide position 3505 and continues up to nucleotide position 3963 (SEQ ID NO: 1) encoding a polypeptide of 152 amino acids (SEQ ID NO: 5).

Both ORF-5 and ORF-6 are translated in the reverse orientation towards the internal repeated sequence. ORF-5 is located between nucleotide positions 4256 and 4897 encoding a polypeptide of 213 amino acids (SEQ ID NO: 1 complementary, SEQ ID NO: 6). ORF-6 is located between nucleotide positions 5138 and 6142 encoding a polypeptide of 334 amino acids (SEQ ID NO: 1 complementary, SEQ ID NO: 7).

The Sau3A site at position 5737 (SEQ ID NO: 1, ORF-6) has also been used as an insertion site for the incorporation of the heterologous β-galactosidase marker gene resulting in a viable virus indicating that this region is not essential for viral infectivity and replication.

Particularly, the mutation introduced into an FHV in order to obtain an FHV mutant according to the present invention is introduced within one or more open reading frames as defined above, preferably in ORF-1, ORF-2, ORF-3 and/or ORF-6.

Surprisingly, it has further been found that the introduction of a mutation into ORF-1 significantly reduces the virulence of the live FHV mutant without affecting the protective properties of the FHV mutant significantly. This finding has offered the possibility to obtain an attenuated FHV mutant, e.g. by introducing a deletion or insertion into the region defined above, which mutant can be administered safely to the animals to be vaccinated in a live form, even via the oro-nasal route.

It will be understood that for the DNA sequence of the FHV genome, natural variations can exist between individual FHV viruses. These variations may result in deletions, substitutions, insertions, inversions or additions of one or more nucleotides. These FHV variants may encode corresponding ORFs that differ from the ORFs disclosed herein. The DNA sequence of such variant ORFs can be located by several methods, including hybridization with the DNA sequence provided in SEQ ID NO: 1, or comparison of the physical map to locate analogous regions comprising said ORFs. Therefore, the present invention provides a section of the FHV genome which allows the introduction of a mutation as defined above, obtainable from any strain of FHV.

Moreover, the potential exists to use genetic engineering technology to bring about the above-mentioned variations resulting in a DNA sequence related to the DNA sequence of the section defined above. It is clear that an FHV mutant comprising a mutation incorporated into said section of the FHV genome characterized by such a related DNA sequence is also included within the scope of the present invention.

In a preferred embodiment of the present invention an FHV mutant is provided wherein the mutation comprises the insertion of a heterologous DNA sequence in the FHV genome.

The heterologous DNA sequence to be incorporated into the FHV genome is a DNA sequence which either does encode a polypeptide different from the polypeptide encoded by the target ORF or is a non-coding DNA sequence, and can be derived from any source, e.g. viral, eukaryotic, prokaryotic or synthetic, including oligonucleotides suitable for the interruption of the expression of the gene products from the ORFs disclosed above.

Such a suitable oligonucleotide may comprise three translational stop codons in each of the possible reading frames in both directions, in addition to one or more appropriate restriction enzyme cleavage sites useful for the insertion of a second heterologous DNA sequence.

In particular, the heterologous DNA sequence encodes an antigen of a significant pathogen for feline species which is able to elicit a protective immune response, said antigen being expressed by the FHV mutant according to the invention upon replication in a host cell.

Preferably DNA sequences encoding an antigen of feline leukemia virus, feline immuno-deficiency virus, feline calicivirus, feline parvo-virus, feline coronavirus and feline Chlamydia are contemplated for incorporation into the section of the FHV genome disclosed herein.

Furthermore, nucleic acid sequences encoding polypeptides for pharmaceutical or diagnostic applications, in particular immuno-modulators such as lymphokines, interferons or cytokines, may be incorporated into said section.

Moreover, as the open reading frames disclosed herein do not display essential functions, one or more of these regions may be deleted partially or completely resulting in the interruption of the expression of an antigenic or functional gene product of the respective open reading frame, if desired followed by the incorporation of a heterologous DNA sequence into the deletion.

An essential requirement for the expression of the heterologous DNA sequence by the FHV mutant according to the invention is an adequate promotor operably linked to the heterologous DNA sequence. It is obvious to those skilled in the art that the choice of a promotor extends to any eukaryotic, prokaryotic or viral promotor capable of directing gene transcription in cells infected by the FHV mutant, e.g. promoters of the retroviral long terminal repeat (Gorman et al., Proc. Natl. Acad. Sci. USA 79, 6777–6781, 1982), the SV40 promotor (Mulligan and Berg, Science 209, 1422–1427, 1980) or the cytomegalovirus immediate early promotor (Schaffner et al., Cell 41, 521–530, 1985).

The technique of in vivo homologous recombination can be used to introduce the heterologous DNA sequence into the FHV genome. This is accomplished by first constructing a recombinant DNA molecule for recombination with FHV genomic DNA. Such a molecule may be derived from any suitable plasmid, cosmid or phage, plasmids being most preferred, and contains a heterologous DNA sequence, if desired operably linked to a promotor. Said DNA sequence and promotor are introduced into a fragment of genomic FHV DNA containing the whole or part of the non-essential section of the FHV genome as defined herein, subcloned in the recombinant DNA molecule.

These so called insertion-region sequences which flank the heterologous DNA sequence should be of appropriate length, e.g. 50–3000 bp, as to allow in vivo homologous recombination with the viral FHV genome to occur. If desired, a construct can be made which contains two or more different heterologous DNA sequences derived from the same or different pathogens said sequences being flanked by insertion-region sequences of FHV defined herein. Such a recombinant DNA molecule can be employed to produce recombinant FHV which expresses two or more different antigenic polypeptides to provide a multivalent vaccine.

Secondly, cells, e.g. feline kidney cells (CRFK) or feline embryo cells can be transfected with FHV DNA in the presence of the recombinant DNA molecule containing the heterologous DNA sequence flanked by appropriate FHV sequences whereby recombination occurs between the insertion-region sequences in the recombinant DNA molecule and the insertion-region sequences in the FHV genome. Recombination can also be brought about by transfecting the infected cells with a nucleic acid sequence containing the heterologous DNA sequence flanked by appropriate flanking insertion-region sequences. Recombinant viral progeny is thereafter produced in cell culture and can be selected for example genotypically or phenotypically, e.g. by hybridization, detecting enzyme activity encoded by a gene co-integrated along with the heterologous DNA sequence or detecting the antigenic heterologous polypeptide expressed by the recombinant FHV immunologically. Recombinant virus can also be selected positively based on resistance to compounds such as neomycine, gentamycin or mycophenolic acid. The selected recombinant FHV can be cultured on a large scale in cell culture whereafter recombinant FHV containing material or heterologous polypeptides expressed by said FHV can be collected therefrom.

In case a deletion mutant according to the invention is desired, either partial or complete deletion of the region from the viral genome identified above can be achieved by the technique of in vivo homologous recombination.

First, a DNA fragment comprising part of the unique short sequence as defined in SEQ ID No.:1 and flanked by at least 100 nucleotides on either side, can be subcloned into a convenient plasmid vehicle.

The deletion to be introduced in the described region can be made in this plasmid by a restriction digest with one or more enzymes of which the sites are correctly positioned in or near the open reading frame. Recircularization of the remaining plasmid molecule would result in a derivative lacking at least part of the coding sequence present within the newly identified region. Alternatively, progressive deletions can be introduced either in one or two directions starting from within a restriction site present within the sequence of an open reading frame. Enzymes such as BalI or endonuclease III can be used for this purpose. Recircularized plasmid molecules are transformed into E.coli cells and individual colonies are analyzed by restriction mapping in order to determine the size of the deletion introduced into the specified region. An accurate positioning of the deletion can be obtained by sequence analysis. The plasmid containing a defined deletion can be cotransfected with FHV viral DNA into cultured feline cells. After in vivo recombination has occured, the deletion will be introduced at the correct position within the described region of the viral genome. Recombinants among the viral progeny can be identified for example by means of 15 to 20 bases long synthetic oligomer which hybridizes specifically to the nucleotide sequence which is generated at the junction where the deletion originally was introduced.

A live FHV mutant according to the present invention, and in particular a live FHV expressing one or more different heterologous polypeptides of specific pathogens, can be used to vaccinate animals, particularly domestic and non-domestic cats or canine species. Vaccination with such a live vector vaccine is preferably followed by replication of the FHV mutant within the inoculated host, expressing in vivo the heterologous polypeptide along with the FHV polypeptides. The polypeptides expressed in the inoculated host will then elicit an immune response against both FHV and the specific pathogen. If the heterologous polypeptide derived from the specific pathogen can stimulate a protective immune response, then the animal inoculated with the FHV mutant according to the invention will be immune to subsequent infection by that pathogen as well as to infection by FHV. Thus, a heterologous nucleic acid sequence incorporated into the insertion-region of the FHV genome according to the invention may be continuously expressed in vivo, providing a solid, safe and longlasting immunity to a pathogen.

An FHV mutant according to the invention containing and expressing one or more different heterologous polypeptides can serve as a monovalent or multivalent vaccine.

For the preparation of a live vaccine the recombinant FHV mutant according to the present invention can be grown on a cell culture of feline origin. The viruses thus grown can be harvested by collecting the tissue cell culture fluids and/or cells. The live vaccine may be prepared in the form of a suspension or may be lyophilized.

In addition to an immunogenically effective amount of the recombinant FHV the vaccine may contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of Bayol F$^{(R)}$ or Marcol 52$^{(R)}$, saponins or vitamin-E solubilisate.

The useful dosage to be administered will vary depending on the age, weight, mode of administration and type of pathogen against which vaccination is sought. A suitable dosage can be for example about $10^{3.0}$–$10.^{7.0}$ pfu/animal.

An FHV mutant according to the invention can also be used to prepare an inactivated vaccine.

For administration to animals, the FHV mutant according to the present invention can be given inter alia intranasally, intradermally, subcutaneously or intramuscularly.

It is a further object of the present invention to produce subunit vaccines, pharmaceutical and diagnostic preparations comprising a heterologous polypeptide expressed by an FHV mutant according to the invention. This can be achieved by culturing cells infected with said FHV under conditions that promote expression of the heterologous polypeptide. The heterologous polypeptide may then be purified with conventional techniques to a certain extent depending on its intended use and processed further into a preparation with immunizing, therapeutic or diagnostic activity.

The above described active immunization against specific pathogens will be applied as a protective treatment in healthy animals. It goes without saying that animals already infected with a specific pathogen can be treated with antiserum comprising antibodies evoked by a FHV mutant according to the invention comprising a heterologous gene derived from the specific pathogen encoding an antigenic polypeptide. Antiserum directed against a recombinant FHV according to the invention can be prepared by immunizing animals, for example cats, with an effective amount of said FHV mutant in order to elicit an appropriate immune response. Thereafter the animals are bled and antiserum can be prepared.

A further object of the present invention is to provide a nucleic acid sequence encoding an FHV polypeptide which can be applied for the preparation of a vaccine for the immunization of feline species against FHV infection and for the preparation of a diagnostic test.

Such a nucleic acid sequence is characterized in that it contains at least part of ORF-1 or ORF-2 encoding a polypeptide having the amino acid sequence as shown in SEQ ID NO: 2 and 3, respectively.

Preferably, the nucleic acid sequence comprises at least part of the DNA sequence of ORF-1 or ORF-2 having the nucleotide sequence located between nucleotide position 127–1281 and 1460–3058 (SEQ ID NO:1), respectively. A nucleic acid sequence according to the present invention can be ligated to various replication effecting DNA sequences with which it is not associated or linked in nature, optionally containing portions of DNA encoding fusion protein sequences such as β-galactosidase, resulting in a so called recombinant DNA molecule which can be used for the transformation of a suitable prokaryotic or eukaryotic host. Such hybrid DNA molecules, are preferably derived from, for example plasmids, or from nucleic acid sequences present in bacteriophages, cosmids or viruses.

In general, prokaryotes are preferred for cloning of DNA sequences in constructing the vectors useful in the invention. For example E.coli K12 is particularly useful. Other E.coli strains may be used include such as DH5A or JM101.

For expression nucleic acid sequences of the present invention are operably linked to expression control sequences. Such control sequences may comprise promoters, enhancers, operators and ribosome binding sites.

The present invention also comprises a polypeptide displaying immunological characteristics of the polypeptide encoded by ORF-1 or ORF-2 having an amino acid sequence as shown in ID NO: 2 and 3, respectively, i.e. the polypeptide comprises one or more immunoreactive and/or antigenic determinants of the polypeptide encoded by ORF-1 or ORF-2, essentially free from the whole virus or other proteins with which it is ordinarily associated.

Immunization of cats against FHV infection can, for example be achieved by administering to the animals a polypeptide according to the invention in an immunologically relevant context as a so-called subunit vaccine.

An alternative to subunit vaccines are live vector vaccines. A nucleic acid sequence according to the invention is introduced by recombinant DNA techniques into a microorganism (e.g. a bacterium or virus) in such a way that the recombinant micro-organism is still able to replicate thereby expressing a polypeptide coded by the inserted nucleic acid sequence.

The FHV polypeptides encoded by ORF 1 or 2 as described above can be used to produce antibodies, both polyclonal, monospecific and monoclonal. Antibodies or antiserum directed against a polypeptide according to the invention have potential use in passive immunotherapy, diagnostic immunoassays and generation of anti-idiotype antibodies.

The invention also relates to an "immunochemical reagent", which reagent comprises at least one of the polypeptides according to the invention or an antigenic fragment thereof.

The term "immunochemical reagent" signifies that the polypeptides according to the invention have been bound to a suitable support or have been provided with a labelling substance.

EXAMPLE 1

Characterization of a New Insertion Reqion in the Unique Short Sequence of the FHV Genome Preparation of FHV DNA and Establishment of a Genomic Library in Lambda Vector EMBL4

The vaccine strain of FHV-1 (commercially available as feline rhinotracheitis virus, strain G2620, from Intervet International B. V.; Holland) was grown on Crandell-Rees feline kidney (CRFK) cells (Crandell, R. A. et al., In Vitro 9, 176–185, 1973) in Glasgow's modified minimum essential medium supplemented with 2.0 g/l tryptose, 2.5 g/l lactalbumin hydrolysate and 5% fetal calf serum. Culture super natants were harvested after full cytopathic effect had developed and virus was concentrated by precipitation with polyethylene glycol (Yamamoto, K. R. et al., Virology 40, 734–744, 1970). DNA was released from virus particles by digestion at 37° C. for two hours with 100 µg/ml proteinase K (Promega, Wisconsin, USA) in a buffer containing 20 mM Tris-HCl (pH 7.5), 10 mM EDTA and 0.5% SDS. After repeated extractions with a 1:1 mixture of phenol/chloroform, nucleic acids were precipitated with two volumes of ethanol and dissolved in TE (10 mM Tris-HCl, pH 7.5, 1 mM EDTA). Viral DNA was partially digested with the restriction enzyme Sau3A (Promega, Wisconsin, USA) according to the conditions recommended by the enzyme supplier and reaction products were separated on a preparative 0.8% agarose gel.

Fragments of the size fraction between 10 and 15 kb were isolated and ligated 2 hours at 15° C. with DNA from bacteriophage lambda EMBL4 digested with BamHI and SalI (Kaiser, K. and Murray, N. in "DNA Cloning", Volume 1, Chapter 1, IRL Press, 1985). Reaction products were packaged in vitro (Promega, Wisconsin, USA) and recombinant phage was plated on E.coli host strain LE392. The library in lambda EMBL4 was enriched for recombinants containing inserts with sequences specifically present in relatively large SalI restriction fragments of the viral genome by screening nitrocellulose replica filters with a $^{32}$P-labelled DNA probe consisting of 10–15 kb restriction fragments isolated by preparative agarose gel electrophoresis of FHV genomic DNA digested with SalI (for technical details see Sambrook, J. et al., in "Molecular Cloning: A laboratory manual", Chapter 2, Cold Spring Harbor Laboratory Press, 1989). Individual recombinants obtained from these screening procedures were amplified and the restriction pattern of the lambda insert DNA was compared with the published map of the complete FHV genome (Grail, A. et al., Arch. Virol., 116, 209–220, 1991). One of the isolates designated λFHV04, was selected for further study and the 13.5 kb insert of this clone (see FIG. 1) was positioned in the unique short segment of the viral genome between unit 0.87 and 0.96 on the map of Grail et al., supra.

EXAMPLE 2

Insertion of a Marker Gene at Restriction Sites in the Unique Short Genome Segment of FHV The 4.8 kb SacI fragment of λFHV04 which was subcloned in pGEM3Z resulting in pFHV13 (see FIG. 2A), revealed a unique BglII restriction site in a suitable position for the integration of a marker gene. The gene used for insertion was derived from pCH110 (Pharmacia, Uppsala, Sweden) by replacing a 72 bp SphI fragment near the SV40 origin of replication by a 12-base double stranded synthetic oligonucleotide containing the recognition sequences for both BamHI and SalI, and single-stranded extremities compatible with the ends generated after digestion of DNA with SphI.

Insertion of the linker between the two SphI restriction sites of pCH110 does not restore the recognition sequence for SphI on either site and creates both a BamHI and SalI site upstream of the SV40 early promotor. Subsequent digestion with BamHI generated a 4.0 kb β-galactosidase expression cassette which was inserted at the BglII site of pFHV13 resulting in pFHV19 (see FIG. 2B). Linearized DNA of plasmid pFHV19 was introduced together with viral DNA into CRFK cells by calcium phosphate-mediated DNA precipitation (Graham, F. L. and v.d. Eb, A. J., Virology 52, 456–467, 1973). One microgram of DNA from pFHVl9 were mixed with 15 microgram of DNA from FHV infected cells in a final volume of 376 µl H$_2$O and added to 500 µl of 2×HBSP (10 mM KCl, 280 mM NaCl, 12 mM glucose, 1.5 mM Na$_2$HPO$_4$, 50 mM HEPES, pH 7.0). Precipitates were formed by gradually adding 124 µl of 1 M CaCl$_2$ solution and incubating the mixtures at room-temperature for 30 minutes.

The suspension of precipitated DNA was gently added to two ø 6 cm dishes containing each a semiconfluent monolayer of CRFK cells in 5 ml of culture medium. After 5 hours, medium was removed and 5 ml of HBSP with 15% glycerol was layered onto the cells. After a one to two minute incubation, the solution was removed, cells were washed with medium and dishes were incubated with overlayers of 0.75% agarose in culture medium. After 3 to 4 days when cytopathic effect started to develop, a second agarose overlay containing the substrate Bluogal (Gibco-BRL, Maryland, USA) with a final concentration of 0.2 mg/ml, was added and plates were incubated until blue plaques were detected. Positive plaques were picked macroscopically and transferred to flasks with fresh CRFK cells in order to amplify the virus. The plating procedure and plaque isolation was continued until homogeneous stocks of recombinant virus had been established. Virus material from the final preparations was used for detailed analysis of the viral genome by Southern blotting and for animal vaccination experiments.

Recombinant FHV containing the β-galactosidase marker gene inserted at the BglII site as present in pFHV13, was shown to be stable upon serial passage in tissue culture on CRFK cells.

A second site in the unique short segment of the FHV genome at which position the β-galactosidase gene could be inserted was mapped in the 5.2 kb BamHI restriction fragment of λFHV04. A subclone containing this fragment in pGEM3Z and designated pFHV10, (see FIG. 3A), was partially digested with the restriction enzyme Sau3A, which has a four-base recognition sequence and generates cohesive DNA extremities compatible with the extremities generated by the enzymes BglII or BamHI. By including 10 μg/ml of ethidium bromide in the Sau3A restriction digest, the digestion of linearized plasmid DNA into smaller fragments was inhibited.

Purification of the full size 7.9 kb linearized DNA of pFHV10 and ligation with the BamHI β-galactosidase expression cassette described above, generated recombinants containing the marker gene inserted randomly at one of the Sau3A restriction sites in pFHV10, including those containing the marker gene in one of the Sau3A sites of the 5.2 kb BamHI insert derived from λFHV04.

Figure 3A:
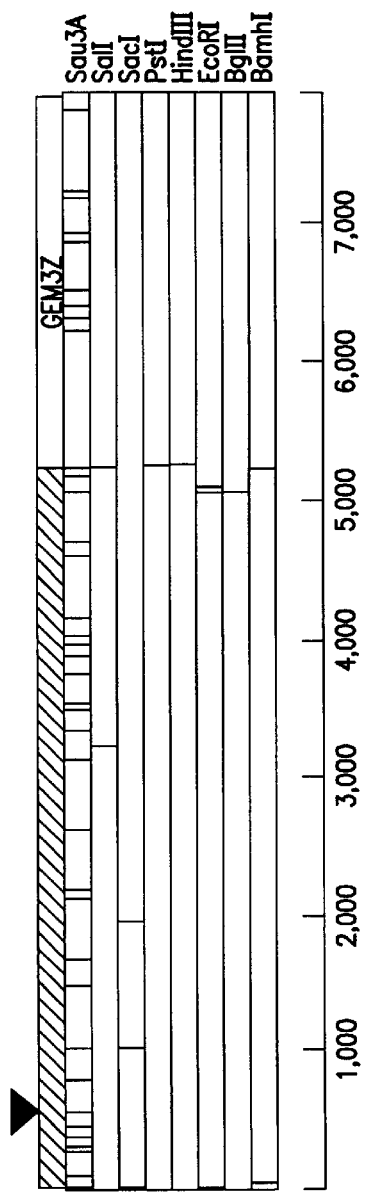
Figure 3B:
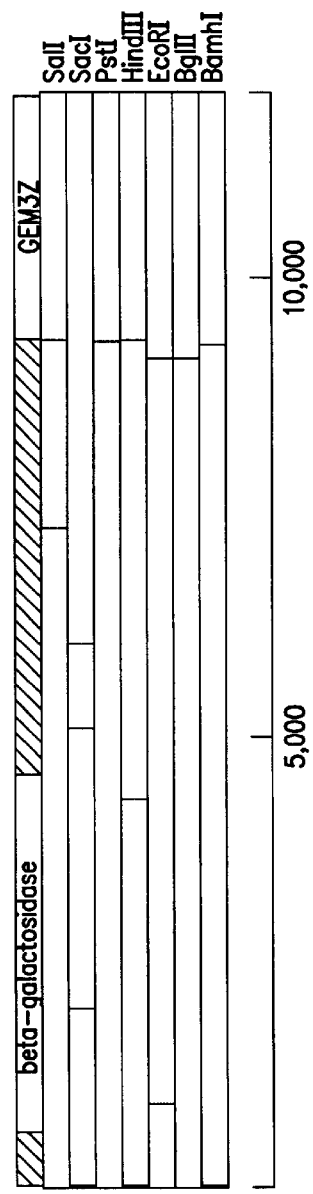

One of the candidates selected from this experiment was shown to contain the marker gene inserted at the Sau3A site indicated in FIG. 3A.

This construct was designated pFHV23 and DNA of this plasmid was transfected with viral DNA into CRFK cells as described previously for pFHV19.

Recombinant FHV expressing β-galactosidase activity could be detected amoung the transfection progeny and these were purified to homogeneity following the procedures described above. Therefore, also the insertion of DNA at a position in the FHV genome corresponding to the Sau3A site indicated in FIG. 3A, does not interfere with functions essential for viral maintenance.

A detailed restriction map was derived from the complete sequence presented in SEQ ID NO: 1 and the exact position of the relevant open reading frames were indicated next to it. The resulting graph which is shown in FIG. 4, revealed several correctly positioned restriction sites both within ORF-2 and ORF-3. However, neither of these sites could be used directly for the insertion of a marker gene since the β-galactosidase expression cassette described in Example 2 is flanked by BamHI sites. The following modifications therefore had to be introduced first. Plasmid pFHV10 (see FIG. 1 and 3a) was chosen for all subsequent manipulations.

The first step consisted in removal of a 0.2 kb Bam HI-BglII fragment between map position 5100 and 5300 (see FIG. 3a) and recircularization of the remaining part with a size of ca. 7.7 kb, thereby suppressing both the BglII and BamHI site originally present in this part of the region. This deletion resulted in plasmid pFHV40 which contained only one BamHI site and none for BglII. Derivatives could now be made based on pFHV40 by insertion of synthetic double stranded linker molecules containing the BglII recognition sequence AGATCT at appropriate positions within the region defined by SEQ ID NO:1.

Two of these positions were selected based on one of the restriction sites either for EcoRV or Spe I, thereby allowing the insertion into ORF-2 and ORF-3, respectively as is shown in FIG. 5. Both enzymes cut at multiple positions in the sequence and the restriction digest therefore was done in the presence of ethidium bromide similar to the procedure described for Sau3A in Example 2, resulting in a majority of linearized full-size plasmid DNA molecules which could be purified by preparative agarose gel electrophoresis. DNA was recircularized by means of synthetic BglII-linkers which were blunt-ended for EcoRV or which contained CTAG-extremities in the case of SpeI digested DNA.

Insertion of the BglII site at the proper position in pFHV40 was verified by restriction analysis. Subsequently, the β-galactosidase expression cassette flanked by BamHI sites was inserted at the newly created BglII site following identical procedures as described in Example 2. Insertion of the marker gen3 into ORF-2 after creating a BglII site which replaced the EcoRV positioned at 2.1 kb (see FIG. 4), resulted in pFHV60 having a restriction map as shown in FIG. 5a. In the case of ORF-3, the marker gene was integrated by means of a BglII site newly created at the SpeI position around 3.1 kb and resulted in pFHV55 with the corresponding map shown in FIG. 5b.

DNA of both pFHV 60 and PFHV 55 was cotransfected with viral DNA into CRFK cells as described previously in Example 2. Recombinant FHV expressing β-galactosidase activity could be detected by Bluogal staining and virus was recovered by single plaque isolation using agarose overlayers. Recombinant viruses were passaged several times in cell culture and were shown to retain the β-galactosidase marker gene stably integrated both for the constructs derived from pFHV60 as well as from pFHV55.

EXAMPLE 3

Structural Analysis of the Insertion Region in the Unique Short Segment of the FHV Genome The nucleotide sequence analysis was performed on relevant parts of the 5.2 kb BamHI and 4.8 kb SacI restriction fragment shown in FIG. 1.

Fragments of λFHV04 were subcloned in both orientations either in pGEM3Z or pSP72 (Promega, Wisconsin, USA).

Progressive deletions were introduced using the enzyme exonuclease III (Henikoff, S., Gene 28, 351–359, 1984) after double digestion of the plasmid DNA with the appropriate restriction enzymes creating a 5'- and 3'-overhanging extremity. The presence of a 3'-overhanging single strand extremity prevented the plasmid vector DNA from being degraded by exonuclease III. Samples of the reaction mixture were taken at 30 seconds intervals and treated according to Henikoff supra., generating recircularized DNA molecules which were transformed into competent E.coli cells. Plasmid DNA from minipreparations of individual colonies were analyzed by restriction mapping for the size of the deletion that was introduced in the original fragment. Series of candidates containing progressive deletions were analyzed by nucleotide sequencing on double stranded DNA in a chain termination reaction using T7 polymerase (Pharmacia, Uppsala, Sweden).

Incomplete or ambiguous readings within the nucleotide sequence were resolved by specific priming of the chain elongation reaction. Sequence data were assembled and analyzed using Gene-Master (Bio-Rad, California, USA) or equivalent software. Assemblage of all data resulted in an about 6.1 kb region (SEQ ID NO:1) within the unique short segment of the FHV genome consisting of six open reading frames encoding the respective polypeptides with amino acid sequences as shown in SEQ ID NO: 2, 3, 4, 5, 6 and 7.

Figure 6:
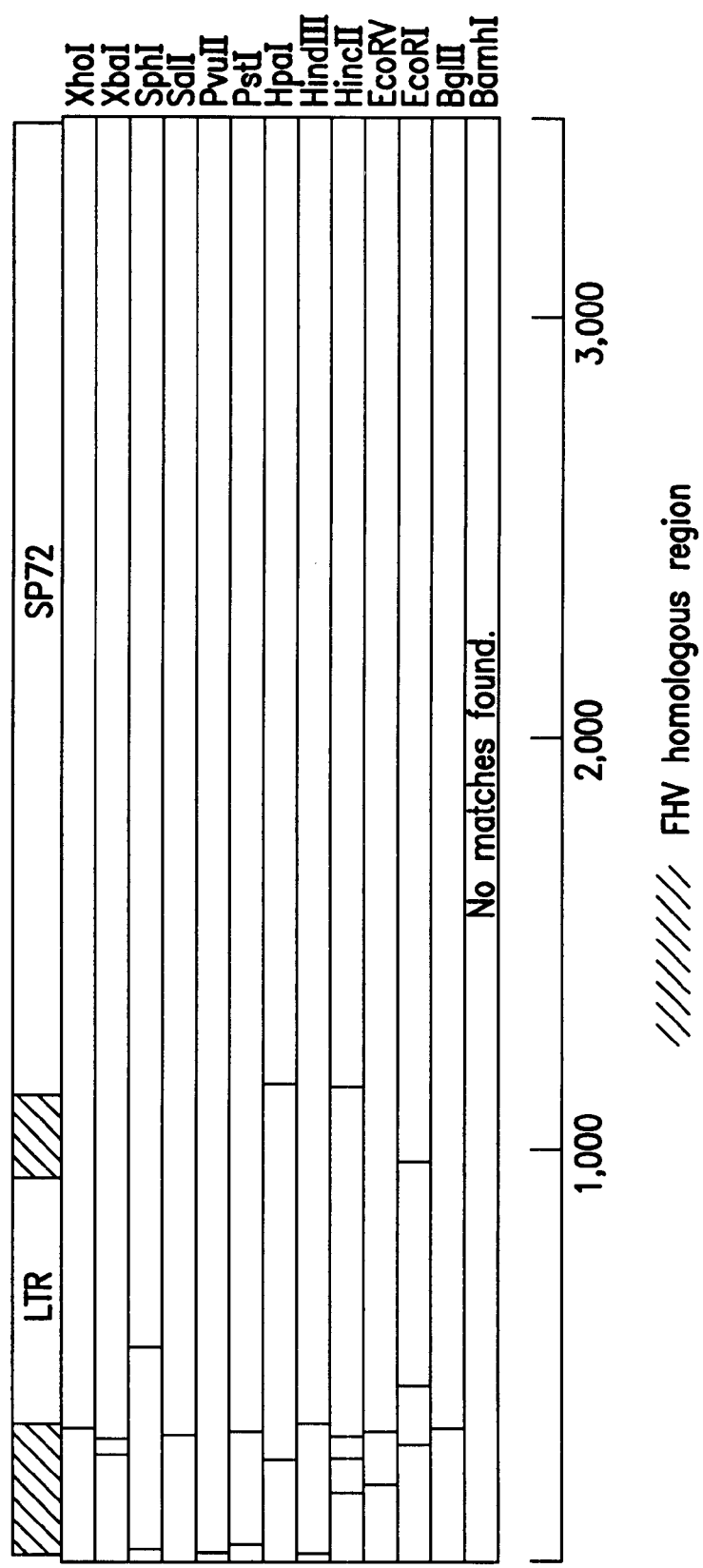

The region of about 6.1 kb, consisting of the six open reading frames including interjacent and flanking, non-translated DNA sequences, can be applied for the insertion of foreign genes into the genome of FHV without disabling essential viral functions necessary for infection and replication.

Particularly the BglII restriction site at nucleotide position 1210 and the Sau3A site at 5737, which were used in Example 2 for the insertion of the β-galactosidase marker gene in pFHV13 and pFHV10, respectively, were shown to be mapping in positions of the FHV genome which are not essential for viral infection or replication.

EXAMPLE 4

Pathogenicity of a FHV Mutant in Infected Animals

A recombinant FHV strain designated C4-1-4-l and containing the β-galactosidase marker gene inserted at the BglII site located within the COOH-terminal region of ORF-1 (see FIG. 1), was selected for evaluation in a cat vaccination trail and compared with the parent FHV strain G2620. The potential of C4-1-4-1 as a new FHV vaccine strain was assessed based on the pathogenecity and the ability of the virus to protect against the clinical signs caused by challenge infection with a virulent FHV strain.

Specific pathogen-free cats 12 weeks of age were infected oronasally with ca. $1 \times 10^5$ $TCID_{50}$ of the FHV mutant or parent strain by applying 0.3 ml per nostril and 0.4 ml in the oropharynx. Animals were observed daily over a period of 2 weeks for clinical signs specific for FHV infection and scored based on the criteria as listed in Table 1. Cats were challenged six weeks after vaccination by oronasal application of $1 \times 10^5$ $TCID_{50}$ of FHV strain SGE (National Veterinary Service Laboratory, USA) and monitored over a period of 2 weeks for clinical signs of FHV infection.

Clinical observations both after vaccination and challenge are summarized in Table 2. Cats in group 1 that had received an oronasal vaccination with strain C4-1-4-1 showed a reduced level in the score for clinical signs compared to the animals in group 2 receiving the parent G2620 strain.

After challenge the vaccinated cats in group 1 still showed a strong reduction in the clinical scores compared to the non-vaccinated controls in group 3.

Therefore it was concluded that the mutant strain C4-1-4-1, had a reduced virulence upon oronasal application in the cat and was still capable of inducing high levels of protection against the clinical signs of a challenge FHV infection.

TABLE 1

| Clin. sign | Severity | Daily Score (points) |
|---|---|---|
| Pyrexia | >39.6–39.9 | 1 |
| | 40.0–40.4 | 2 |
| | 40.5–40.9 | 3 |
| | >41.0 | 4 |
| Sneezing | infrequent | 1 |
| | frequent | 2 |
| | paroxysmal | 3 |
| Cough | infrequent | 1 |
| | frequent | 2 |

TABLE 1-continued

| Clin. sign | Severity | Daily Score (points) |
|---|---|---|
| Respiration | URT noise | 1 |
| | stertor | 1 |
| | mouth breathing | 2 |
| Salivation | | 2 |
| Conjunctivitis | mild | 1 per eye |
| | moderate | 2 per eye |
| | severe | 3 per eye |
| Ocular discharge | serous | 1 per eye |
| | mucopurulent | 2 per eye |
| Nasal discharge | serous | 1 per nostril |
| | mucopurulent | 2 per nostril |
| Ulceration | nasal | 2 |
| | nasal/bleeding | 3 |
| | oral | 2 |
| | oral/bleeding | 3 |
| Oral erythema | | 1 |
| Inappetance | | 1 |
| Depression | | |

TABLE 2

| group | vaccine | animal code | Clin. scores post-vaccination individual score | Clin. scores post-vaccination average | Clin. scores post-challenge individual scores | Clin. scores post-challenge average |
|---|---|---|---|---|---|---|
| 1 | C4-1-4-1 | 40 O | 6 | 1.7 | 14 | 12.0 |
| | | 40 Q | 0 | | 9 | |
| | | 40 Y | 0 | | 11 | |
| | | H 16 | 1 | | 14 | |
| 2 | G 2620 | 40 V | 1 | 7.0 | 1 | 5.5 |
| | | 40 W | 8 | | 7 | |
| | | 40 X | 5 | | 6 | |
| | | H 18 | 14 | | 8 | |
| 3 | none | H 14 | — | — | 77 | 79.7 |
| | | H 12 | — | | 85 | |
| | | H 11 | — | | 69 | |
| | | B 39 | — | | 88 | |

EXAMPLE 5

Construction of Recombination Plasmid for the Insertion of Heterologous Genes into the Genome of FHV The recombination plasmid used for the insertion and subsequent expression of foreign genes in FHV was based on the BglII restriction site at nucleotide position 1210 (SEQ ID NO: 1) and mapped in ORF-1 (FIG. 1). The 5.2 kb BamHI fragment from λFHV04 was thereto subcloned in the BglII site of pSP72 (Promega, Wisconsin, USA) such that the orientation of ORF-1 was identical to the orientation of the T7 RNA polymerase promotor of the plasmid vector. This construct, designated pFHV11, was submitted to the uni-directional deletion technique using the enzyme exonuclease III and following similar procedures as described in example 3 for the nucleotide sequence analysis. This resulted in pFHV27 which contains a remaining 0.4 kb from the original 5.2 kb BamHI fragment with the unique BglII site positioned about in the middle and with sufficient flanking FHV genomic sequences in order to allow the in vivo recombination with the viral genome.

A strong promotor which could direct the expression of foreign genes after their insertion into the genome of the FHV virus was selected from the LTR sequence of Rous sarcoma virus (RSV). The promotor has been mapped on a 580 bp NdeI/HindIII restriction fragment from pRSVcat (Gorman, C. M. et al., Proc. Natl. Acad. Sci. USA 79, 6777–6781, 1982) and was inserted between the HindIII and PstI sites of pGEM3Z by means of double stranded synthetic linkers on both sides of the fragment. The connection between the HindIII site from the vector pGEM3Z and the NdeI site of the RSV fragment carrying the LTR promotor was made with a 30 bp linker containing cohesive ends compatible with HindIII on one and NdeI on the other site. However, after ligation both restriction sites are not restored due to deliberate modifications in the outer nucleotides of the six base pair recognition sequence. In addition to the removal of these two sites, a new restriction site (BamHI) present within the linker itself was created at the corresponding position. A second 20 bp linker was synthesized which connected the HindIII site from the LTR fragment to the PstI site from pGEM3Z, in this case without destruction of the recognition sequence on either of the ends and adding the convenient restriction sites BglII and XhoI, to those already present in the polylinker of pGEM3Z. The resulting derivative, designated pVEC01, therefore contains a 650 bp restriction fragment carrying the LTR promotor sequence immediately followed by multiple restriction sites available for the insertion of foreign genes. The 650 bp fragment is flanked on either end by a BamHI restriction site and has been transferred as such to the unique BglII site present in pFHV27. The cohesive ends generated by these two restriction enzymes are compatible but ligation does not restore either of the original recognition sequences for BglII or BamHI. The resulting constructs was designated pFHV38 and checked by restriction mapping (FIG. 6). The structure of this FHV recombination vector allows the insertion of foreign genes immediately downstream of the LTR promotor and subsequent integration of the complete expression cassette into the FHV genome by in vivo recombination. The positions of the different restriction sites downstream of the LTR, in particular those for the enzymes BglII and SalI, are designed in such a way that even multiple gene insertion can be envisaged.

What is claimed is:

1. an isolated feline herpesvirus (FHV) mutant, comprising one or more mutations in open reading frames (ORFs) 1, 2 or 3, said ORFs being contained within the DNA of FHV having the restriction map shown in FIG. 1, and wherein said mutations are such that the FHV mutant fails to produce functional polypeptide corresponding to the ORF or ORFs so mutated.

2. The FHV mutant of claim 1, wherein said ORFs 1, 2 and 3 code for the amino acid sequences of SEQ ID NOs: 2, 3 and 4, respectively.

3. The FHV mutant of claim 1, wherein said one or more mutations comprises an insertion of a heterologous DNA sequence.

4. The FHV mutant of claim 3, wherein said DNA sequence encodes a polypeptide and is under the control of a promoter regulating the expression of said polypeptide in a cell infected with said FHV mutant.

5. The FHV mutant of claim 4, wherein said heterologous DNA sequence encodes an antigen of a feline pathogen.

6. The FHV mutant of claim 5, wherein said feline pathogen is selected from the group consisting of feline leukemia virus, feline immunodeficiency virus, feline calicivirus, feline parvovirus, feline coronavirus and feline chlamydia.

7. The FHV mutant of claim 1, wherein said one or more mutations comprises a deletion.

8. A vaccine comprising an FHV mutant that has a mutation in open reading frame (ORF) 1 or its regulatory elements, which is contained within the DNA of FHV having the restriction map shown in FIG. 1, said mutation being such that said FHV mutant fails to produce a functional ORF 1 polypeptide, and a pharmaceutically acceptable carrier.

9. The vaccine of claim 8, wherein said mutation comprises a deletion of a heterologous DNA sequence.

10. The vaccine of claim 8, wherein said mutation comprises an insertion of a heterologous DNA sequence.

11. The vaccine of claim 10, wherein said DNA sequence encodes an antigen of a feline pathogen.

12. The vaccine of claim 11, wherein said feline pathogen is selected from the group consisting of feline leukemia virus, feline immunodeficiency virus, feline calicivirus, feline parvovirus, feline coronavirus and feline chlamydia.

13. The vaccine of claim 8, wherein said FHV mutant further comprises an insertion of a heterologous DNA sequence in ORFs 2 or 3.

14. The vaccine of claim 13, wherein said DNA sequence encodes an antigen of a feline pathogen.

15. The vaccine of claim 14, wherein said feline pathogen is selected from the group consisting of feline leukemia virus, feline immunodeficiency virus, feline calicivirus, feline parvovirus, feline coronavirus and feline chlamydia.

16. A vaccine comprising an attenuated FHV strain that has a further mutation in at least one of ORF 2 and ORF 3, said ORFs being contained within the DNA of FHV having the restriction map shown in FIG. 1, wherein said mutation is an insertion of a heterologous DNA sequence, together with an acceptable carrier.

17. The vaccine of claim 16, wherein said DNA sequence encodes an antigen of a feline pathogen.

18. The vaccine of claim 17, wherein said feline pathogen is selected from the group consisting of feline leukemia virus, feline immunodeficiency virus, feline calicivirus, feline parvovirus, feline coronavirus and feline chlamydia.

19. A marker vaccine comprising an attenuated FHV strain that has a deletion or insertion mutation in at least one of ORF 1, ORF 2 and ORF 3, said ORFs being contained within the DNA of FHV having the restriction map shown in FIG. 1, together with an acceptable carrier.

20. An isolated nucleic acid fragment of the DNA of the FHV genome that has the restriction map depicted in FIG. 1, which is of a length sufficient to allow for in vivo homologous recombination with a viral FHV genome, and which contains a mutation in at least one of ORF 1, ORF 2 and ORF 3, said mutation being such that no corresponding functional protein is expressed.

21. The nucleic acid fragment of claim 20, which further comprises a heterologous DNA sequence, said DNA sequence being inserted into the nucleic acid fragment in such a way that it is flanked by a sufficient number of base pairs on each side to allow for homologous recombination.

22. A recombinant DNA molecule, comprising the nucleic acid fragment of claim 20.

23. A host cell transformed with the recombinant DNA molecule of claim 2.

24. A recombinant DNA molecule, comprising the nucleic acid fragment of claim 21.

25. A host cell transformed with the recombinant DNA molecule of claim 24.

26. A cell culture infected with the FHV mutant of claim 1.

27. A method of immunizing a cat against FHV, comprising administering an effective amount of the vaccine of claim 8.

28. A method of immunizing a cat against FHV, comprising administering an effective amount of the vaccine of claim 16.

29. A method of immunizing a cat against FHV, comprising administering an effective amount of the vaccine of claim 19.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 6154 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Feline herpesvirus (FHV-1)
      (B) STRAIN: G2620

(vii) IMMEDIATE SOURCE:
      (B) CLONE: Lambda FHV04

(ix) FEATURE:
      (A) NAME/KEY: CDS
      (B) LOCATION: 127..1281
      (D) OTHER INFORMATION: /label= ORF-1

(ix) FEATURE:
      (A) NAME/KEY: CDS
      (B) LOCATION: 1460..3058
      (D) OTHER INFORMATION: /label= ORF-2

(ix) FEATURE:
      (A) NAME/KEY: CDS
      (B) LOCATION: 3055..3357
      (D) OTHER INFORMATION: /label= ORF-3

(ix) FEATURE:
      (A) NAME/KEY: CDS
      (B) LOCATION: 3505..3963
      (D) OTHER INFORMATION: /label= ORF-4

(ix) FEATURE:
      (A) NAME/KEY: CDS
      (B) LOCATION: complement (4256..4897)
      (D) OTHER INFORMATION: /label= ORF-5

(ix) FEATURE:
      (A) NAME/KEY: CDS
      (B) LOCATION: complement (5138..6142)
      (D) OTHER INFORMATION: /label= ORF-6

-continued (xi) SEQUENCE DESCRIPTION: SEQ ID NO:1:

```
GTCCACATTC CAATCGAGTT GGTAGGGAAG ATATGAAGTG GGCGGTACCA ACCATCATAA      60

AATAGGTTGG AGTCTGGACC AACGTTCACT CTTTTGAGTG TAAAGGACCA CAGCATAATA     120

CTTAATATGT CGTCGATAGC CTTCATCTAT ATATTGATGG CGATTGGAAC AGTTTATGGG     180

ATTGTGTATC GTGGAGATCA TGTAAGTCTT CATGTTGATA CAAGCTCCGG CTTTGTAATA     240

TATCCAACAC TGGAGAATTT TACGATCTAC GGCCATCTAA TCTTTCTCGA CGACCAACCA     300

TTACCAGTAA ACAATTATAA TGGAACCCTC GAGATTATAC ATTACAACCA TCACTCTTCT     360

TGCTATAAAA TCGTTCAAGT AATAGAATAT TCATCATGTC CACGTGTACG CAATAATGCT     420

TTCCGGTCCT GTCTCCACAA GACCTCTATG CACCAATACG ATCAGCTTTC CATAAACACA     480

TCCGTTGAAA CGGGGATGTT ATTGACAATA ACATCTCCGA AAATGGAAGA TGGTGGAATC     540

TACGCACTGC GGGTAAGATT TAACCATAAT AACAAAGCTG ATGTATTTGG CCTTTCGGTG     600

TTTGTTTACT CATTCGATAC GCGTGGTCAT CGACATCATG CGGACGAAAA TTTGAATGGT     660

GAAATTCTTA CTACTCCATC ATCGATGAAA CATATGTTA AAGTTAACAC ACCAATATAT     720

GATCATATGG TGACAACTCA AACAACTTCT AATAAATCGA TGGAGTCTGA ACCATCAAAT     780

ACATCAATAT CATGCCATAC ATTTCAAAAT GACCCGAATG AGGGTGAGAC TTTATATACA     840

CACTTATTGA ACATCGCTGG AAATATAACA TATGATGACA TGGTTATGGA TGGCACCACA     900

TTGCAACCCA GATTAATCGA TATGGGACTT AACTTGTCTG TTACATCTTC CTTTAAAAAT     960

GAAACCACGC AAAAATGGAC ACCAGACAGA AAGGTGGGTT TTGTTATAGT AATCTCAATC    1020

GCAGTTTTAC TACTCCTTGC GGTCATCGGA TCCATCATCA ATAGTGCAAT ACGCAAGCAT    1080

ATAATGGTCT GTGCTGGGCG GCGGATCTAT ATACCAAACA ACGATGGGCG ACCATCAACG    1140

GAAATGACAC GGTTTACTCG CCAGACTAAA CCATCGAATT CGAGTTCCAA GTCCCTACTC    1200

GATGTCCCCA GATCTTCGAA TTCCACCCCA ACCGATGGCG TCTCTAGAAG TCAGTTAACC    1260

GTAATTAACG AAGAAACCTA ATATATTTAT AAACAAATAA AATACTTTTA AAAATGGATA    1320

TCTGGTCATG TGTAATGTTG ACGCATAGTG GGTGGTGACC TAAGATTATA TTAAAATGTA    1380

GAAGGTTTTA TGCCCAGTTC ACAGTATCTA CTGTGACCTA CCCCGGGGTG GTAATAACAA    1440

TACTATCGAA TAGCCAACAA TGGGACTGCT TGTTACCATC CTCGTGATAT TATTGATTGT    1500

TACTTCATCA AGTTCTACTA TTCATCAAGT AACGATGACA GAAGGTGCCG CACTTTTAGT    1560

CGATGGGGAT GGGATCGACC CACCTTTAAA CAAAACTTCA CATTTTTTGC GAGGTTGGAC    1620

ATTTCTAGAG ACTCCGAAAG GATGTACAGG AGAGGTGAGT GTTCTAAAAG TATGTATAGA    1680

TCGTGGGGTA TGTCCGGATG ATATCGTTAT AAATAAGAGA TGTGGTCACA AAATGCTTGA    1740

AACCCCACTA GCGTTGGCGG AACTTGGAAT TTCTAATAGT CTCTCATCA GAACCAAAGA    1800

CGTATATTTC GTGAATAAGA CCGTGTTTCC AATTCTCACA CCCGAAAAAA GTGGCCTTGG    1860

TATTCAGGGG GCCACTACGA ATATATCCGG GATATATACC CTGCATGAGC ACGGTGATAA    1920

TGGATGGAGT CATCAATCTA CATTTTTTGT GACCGTAAAG GCAAAACATC CCGGACCATC    1980

GTTAACCCCA GCACCGGTTC ACTTAATAAC ACCACATCGC CATGGGCAC ATTTCCACGT    2040

AAGAAACTAT CATTCGCATG TCTACATTCC GGGAGATAAG TTCTTATTAG AAATGCACCT    2100

CAAATCAGAT ATCTATGATC CAGAATTTTC AGCAACAATA GACTGGTATT TTATGGAGAC    2160

TGATATAAAA TGCCCAGTTT TTAGAATTTA TGAAACTTGT ATATTTCACC CCATGCCGC    2220

ATCCTGTCTA CATCCGGAAG ATCCCTCATG CAGTTTTACA TCACCACTTC GAGCGGTATC    2280

TTTAATTAAT AGATTTTATC CAAAATGCGA TCACAGATAT GCCGATTGGA CATCCAGATG    2340
```

-continued

```
TATCAACACT CCAAGTATAA ATCATATGCC ATATATCGAA CAGCCGGCCA ATAACGTGGA    2400

TCTAAAGTTT ATCAATGTAC CCACCAACGC TTCTGGGTTG TACGTATTCA TACTTCGTTA    2460

TAATGGACAT CCGGAAGAAT GGACCTATAC ACTCACATCA ACAGGAGCTA AATTTTTGAA    2520

TGTGATTAGG GATCTGACAC GCCCACGTCT TGGTAGTCAT CAAATAGAGA CCGATATTAG    2580

CACATCTTCG CAGTCGCCTA CCACGGAGAC ACCACGAAAC ATACATATAA CGTGGGCGAG    2640

ACGTTATCTA AAGGTTATCA TAGGAATAAT TTGCGTAGCT GGTATCCTTT TGATTGTAAT    2700

CTCTATCACA TGTTATATTC GATTTCGTCA TATGCGATAT AAACCATATG AAGTGATCAA    2760

CCCATTCCCT GCGGTATATA CCAGCATTCC TAGTAACGAT CCCGACGAAC TCTACTTTGA    2820

ACGTATCGCA TCGAACGACG AAGAATCGGC AGATGATTCT TTTGATGAAT CAGATGAGGA    2880

GGAGCCATTG AATAATCATC ATATTTCAAC AACCCAACAT ACTGATATTA ATCCAGAAAA    2940

ATCCGGATCT GGGTACAGTG TATGGTTTCG TGATACAGAA GATACATCAC CTCAGCCCCT    3000

ACACGCTCCT CCAGATTACA GTCGCGTAGT TAAAAGATTA AAGTCTATTT TAAAATGACC    3060

CGTCGACGAG TTCTAGCACC ACGGGAATTG GAAGCTGCTC GTAAACTCCG TGAGATTTTC    3120

AACGCAGAGT ACGTCGCACC TACGTTCACA CTAGTCGATC CGGGGATAC GTCAAACGCG     3180

TATATTGTAT GTAGGACCCC GGTGACCGAA GTAGTCTCTT CCATATCAAG AGGTATCGAC    3240

AATAGAAAAT CGGTAGATTC TTCATTTATT CGAATCGTCA GTAAATTAAT CATTAGGAAT    3300

GCTATTCACA TGGGACTATC CGTCCTATGT GCATTTATAT CCTATAATAA ACCATGATAA    3360

ATTTTATGTG GATATTTTAT TAATCCTCCA AACCGTATGG GGGAGCACTT TTATAGAAAT    3420

CTACCATAGA GAGTATATCC GTTAAATACC CGGGTTTGAT TATATGTTTG TCAGTTGGTA    3480

GTTGAACTTC CATCGCCATC TAAGATGGAC CATCAAACAT CACTTATTAA TGCCACAGAT    3540

GATAATTGCT TAGACACGGA TTCTAGTATA AACTTGCCAA GCATAGATAA ATGCGAAATT    3600

GATGACAATT CAATTGCGGA TGAAACTCTA TCCGACAAGG GCTCCCCGGT CGCTATACCG    3660

CTATGCGCCA CCATCGAGAT CCCGCGTGGG AATGCGGACC GGCAGTCCCC AAGCCACGAC    3720

GTACGAGGGG CCAATAGGAC AAATTACGAC TCCGATACCG GCTGTTATTA TAGCGAGAGT    3780

GACAACGAGA CGGCGACGCT GTTCATAAAT AGAATAGGCA AACGCGAGAC GGCCAAGAGA    3840

CGGCGACGGA GGCGGTGTCT GGTGGCACTG GCCGTCTCAG GGGTGGCGAC ACTATGCGTG    3900

CTATCGGGAT TATTAGGTGC GCTGCTGTGG CGGCTGATGG ATGCCCCCGG GACGCGCCGG    3960

TGACGGGCTC GTTCAATAAA CATAGCATAC GTTATGACAT GGTCTACCGC GTCTTATATG    4020

GGGACGATTG TTTTAGATTG GGTTTTCAGC GAGGCGCGTA CAATATTGTA CAGGGGAGTC    4080

TCCACGAACC CTAGGTTTTG GGTCGTAGAT CACCACGGGG AGGGGATAGG GTACGAGTAC    4140

ATAAATCTTG TTGCTGGGAT CGATCGTGTG ATAAAGAATT TTGAGACCTT AGATGGCTTA    4200

TGAAGGCGAG TTTATTTAGA TTAGTGGGGA GAGATGGGGA GAAAACGGGG GTCTTCTACT    4260

TCTCAATATT CGGTATACAC CCCCCATAGT TTCTCCGCTG TAGATAAACC GCGGCTGCCG    4320

CGTGTTTCAC CAGGAGCTCC GGTTCGTCGA GCACCATCTC GTATAGCGCG TTCCAGTGAG    4380

CTACGGCATC CGCAGGGGGG ATTTCCCCGG CCCCGAAACC CTCTTCGAAA AACCGCCGAC    4440

AGGCATCCTC ATAGATGTGG GAGTGGGTGC ATGTAGCCGC GTGACCCAGA CAACACCAAT    4500

AGGCGCAGTA GAGGAGGCGG GTGTGTAGCT CCGGATGGGA TTCTGGTTTT GCGGGTCCCA    4560

GACCCATGAG ATAACGGCCT ACCAGGTGCC GTATGGGATC GGCGACGTGA AATGGGCTAC    4620

CCCCGCTACC CTCCATGGAG CGTGAGTAGC TTCGAAATAC CTCACGATAC TGCCGATATA    4680
```

-continued

```
CCCCGGGCCA TATGTCCGCG GGTGGGGGAC CACCGAGGCG CATGAGGCAG AAGGCCTCAC    4740

ACGACGCGAC CCGGAGAGCG TCGAACAGAG CCCTGACAGA ACGAGGTAGC GTTTCCGCGT    4800

GATCCGCGGA GTCCCCCCTC AGGGGGTACA TCTCCATCTC CGCGACACCA GTCATGTTAA    4860

AGGACTCGAT GTTAGTGTCT TCCCAGCGAC GGTTCATGAT ATACGCGTCC GCTGGAGTCT    4920

AGTGGACTCC CATAGGAGTC GGGCGTCGTG TAGGAATGTA TATATCGGGG GGTATTACAC    4980

CAACTATATG GTCCGTGATT ATCCGGGCTA TGTACTCATC ATGAGAGACA GGGGTTGGGG    5040

TGTGGGTAAT AAATCTATTG CACCTAGGTA AGGTGGAAAG GAATCAGGAG GCGGTTGTGA    5100

GACATGTGGT TTCCTATATA CCTTTTTAAT TTGATATCTA CATCCTCTTC CGTTTGGCCG    5160

CGTGGCGCGC GCTCCTTCTG ACGGGATTAC ATCTGCGTTT TTTACCACAG ACACGGGTAC    5220

CATAATCAAC GTCAGAACTA TCCGACTCTG ACGAACTAGA GCTCCGATCC TCCGTTTCAT    5280

CCGAGTCGTC ATCCGTCCCA GAATCTGAGT CACTGGTACT AGTCTCGTCC CCATCACCCC    5340

CCACATAACT AAATTCGGAC AACGATGTCT CTCCACAATC CGAATCGCTA CTTTCTATAT    5400

CCACCCCCTC ACCATCTTCA GAGTCTTCGC TACCACTAAC ATCACATTCC TGTCCAAATA    5460

AAATCGGGGG GACCTGTGTG GGAGGCTCAA GGAACCGCCG ATCGCATGGT TCAGTGGTAT    5520

TGAGGTGGCG TAAGGTGGCT CGCAGGGGAC GAGCCTGTTC CGAAGACAAC TGTAAGAGGG    5580

TCTCCCAACA GGCTCTGGTC GGACGTTGGT TCGTATAACC CATGATATAA AAGTCTAACA    5640

ACGCCCGACG AAGCGCGCGG GAATCCGAGC TGACATTTAC GGACGACGTG GCTATACATC    5700

TGAACATGAT GTTGACATCT TTCATCAGCC GTTTTAGATC ACATCGCCAC GGTGGGGAAC    5760

AAAAAGCCCC GGGTCCGTGT GTCAAATAAG CTCTGAGGTC ACGACTCGCG ACCACGCTTC    5820

CATACTCGGG ATGATCATCC CCATCGGGAA GTGTCGCGGG AGCGCGCACC GGACTCGTAT    5880

CATCAGTTTC TACGCAAGAA ACGGGTATCT TTGATCCTCC TGGTGTTTGC GATGCGAAGG    5940

TCGATGAACC GGTCGATGGT GTTAACGAGG GGAGGATGGG ACTGGGATCT ATATTCAACC    6000

CCCCACGGGG TCGCAGTCTA CACGATCCGT CGCATAGACC ACAGGGTTGT CCATGACCCA    6060

ATCGACCGCT CCTGAGTTCT GGGGGTTTTA CAGCGGCGGG GGTCGTATGT GGCCTACCGC    6120

GATGCTTCCT TCCCTTCGCC ATGGGACTCC CTGG                               6154
```

(2) INFORMATION FOR SEQ ID NO:2:

(i) SEQUENCE CHARACTERISTICS:
        (A) LENGTH: 384 amino acids
        (B) TYPE: amino acid
        (D) TOPOLOGY: linear (ii) MOLECULE TYPE: protein (ix) FEATURE:
        (D) OTHER INFORMATION: /label= ORF-1

(xi) SEQUENCE DESCRIPTION: SEQ ID NO:2:

```
Met Ser Ser Ile Ala Phe Ile Tyr Ile Leu Met Ala Ile Gly Thr Val
  1               5                  10                  15

Tyr Gly Ile Val Tyr Arg Gly Asp His Val Ser Leu His Val Asp Thr
                 20                  25                  30

Ser Ser Gly Phe Val Ile Tyr Pro Thr Leu Glu Asn Phe Thr Ile Tyr
             35                  40                  45

Gly His Leu Ile Phe Leu Asp Asp Gln Pro Leu Pro Val Asn Asn Tyr
         50                  55                  60

Asn Gly Thr Leu Glu Ile Ile His Tyr Asn His His Ser Ser Cys Tyr
 65                  70                  75                  80
```

```
Lys Ile Val Gln Val Ile Glu Tyr Ser Ser Cys Pro Arg Val Arg Asn
                85                  90                  95

Asn Ala Phe Arg Ser Cys Leu His Lys Thr Ser Met His Gln Tyr Asp
            100                 105                 110

Gln Leu Ser Ile Asn Thr Ser Val Glu Thr Gly Met Leu Leu Thr Ile
        115                 120                 125

Thr Ser Pro Lys Met Glu Asp Gly Gly Ile Tyr Ala Leu Arg Val Arg
    130                 135                 140

Phe Asn His Asn Lys Ala Asp Val Phe Gly Leu Ser Val Phe Val
145                 150                 155                 160

Tyr Ser Phe Asp Thr Arg Gly His Arg His His Ala Asp Glu Asn Leu
                165                 170                 175

Asn Gly Glu Ile Leu Thr Thr Pro Ser Ser Met Glu Thr Tyr Val Lys
            180                 185                 190

Val Asn Thr Pro Ile Tyr Asp His Met Val Thr Thr Gln Thr Thr Ser
        195                 200                 205

Asn Lys Ser Met Glu Ser Glu Pro Ser Asn Thr Ser Ile Ser Cys His
    210                 215                 220

Thr Phe Gln Asn Asp Pro Asn Glu Gly Glu Thr Leu Tyr Thr His Leu
225                 230                 235                 240

Leu Asn Ile Ala Gly Asn Ile Thr Tyr Asp Asp Met Val Met Asp Gly
                245                 250                 255

Thr Thr Leu Gln Pro Arg Leu Ile Asp Met Gly Leu Asn Leu Ser Val
            260                 265                 270

Thr Ser Ser Phe Lys Asn Glu Thr Thr Gln Lys Trp Thr Pro Asp Arg
         275                 280                 285

Lys Val Gly Phe Val Ile Val Ile Ser Ile Ala Val Leu Leu Leu Leu
    290                 295                 300

Ala Val Ile Gly Ser Ile Ile Asn Ser Ala Ile Arg Lys His Ile Met
305                 310                 315                 320

Val Cys Ala Gly Arg Arg Ile Tyr Ile Pro Asn Asn Asp Gly Arg Pro
                325                 330                 335

Ser Thr Glu Met Thr Arg Phe Thr Arg Gln Thr Lys Pro Ser Asn Ser
            340                 345                 350

Ser Ser Lys Ser Leu Leu Asp Val Pro Arg Ser Ser Asn Ser Thr Pro
        355                 360                 365

Thr Asp Gly Val Ser Arg Ser Gln Leu Thr Val Ile Asn Glu Glu Thr
    370                 375                 380

(2) INFORMATION FOR SEQ ID NO:3:

(i) SEQUENCE CHARACTERISTICS:
        (A) LENGTH: 532 amino acids
        (B) TYPE: amino acid
        (D) TOPOLOGY: linear (ii) MOLECULE TYPE: protein (ix) FEATURE:
        (D) OTHER INFORMATION: /label= ORF-2

(xi) SEQUENCE DESCRIPTION: SEQ ID NO:3:

Met Gly Leu Leu Val Thr Ile Leu Val Ile Leu Leu Ile Val Thr Ser
 1               5                  10                  15

Ser Ser Ser Thr Ile His Gln Val Thr Met Thr Glu Gly Ala Ala Leu
            20                  25                  30
```

-continued

```
Leu Val Asp Gly Asp Gly Ile Asp Pro Pro Leu Asn Lys Thr Ser His
         35                  40                  45

Phe Leu Arg Gly Trp Thr Phe Leu Glu Thr Pro Lys Gly Cys Thr Gly
         50                  55                  60

Glu Val Ser Val Leu Lys Val Cys Ile Asp Arg Gly Val Cys Pro Asp
 65                  70                  75                  80

Asp Ile Val Ile Asn Lys Arg Cys Gly His Lys Met Leu Glu Thr Pro
                 85                  90                  95

Leu Ala Leu Ala Glu Leu Gly Ile Ser Asn Ser Ser Leu Ile Arg Thr
                100                 105                 110

Lys Asp Val Tyr Phe Val Asn Lys Thr Val Phe Pro Ile Leu Thr Pro
         115                 120                 125

Glu Lys Ser Gly Leu Gly Ile Gln Gly Ala Thr Thr Asn Ile Ser Gly
     130                 135                 140

Ile Tyr Thr Leu His Glu His Gly Asp Asn Gly Trp Ser His Gln Ser
145                 150                 155                 160

Thr Phe Phe Val Thr Val Lys Ala Lys His Pro Gly Pro Ser Leu Thr
                165                 170                 175

Pro Ala Pro Val His Leu Ile Thr Pro His Arg His Gly Ala His Phe
                180                 185                 190

His Val Arg Asn Tyr His Ser His Val Tyr Ile Pro Gly Asp Lys Phe
        195                 200                 205

Leu Leu Glu Met His Leu Lys Ser Asp Ile Tyr Asp Pro Glu Phe Ser
        210                 215                 220

Ala Thr Ile Asp Trp Tyr Phe Met Glu Thr Asp Ile Lys Cys Pro Val
225                 230                 235                 240

Phe Arg Ile Tyr Glu Thr Cys Ile Phe His Pro His Ala Ala Ser Cys
                245                 250                 255

Leu His Pro Glu Asp Pro Ser Cys Ser Phe Thr Ser Pro Leu Arg Ala
                260                 265                 270

Val Ser Leu Ile Asn Arg Phe Tyr Pro Lys Cys Asp His Arg Tyr Ala
        275                 280                 285

Asp Trp Thr Ser Arg Cys Ile Asn Thr Pro Ser Ile Asn His Met Pro
290                 295                 300

Tyr Ile Glu Gln Pro Ala Asn Asn Val Asp Leu Lys Phe Ile Asn Val
305                 310                 315                 320

Pro Thr Asn Ala Ser Gly Leu Tyr Val Phe Ile Leu Arg Tyr Asn Gly
                325                 330                 335

His Pro Glu Glu Trp Thr Tyr Thr Leu Thr Ser Thr Gly Ala Lys Phe
             340                 345                 350

Leu Asn Val Ile Arg Asp Leu Thr Arg Pro Arg Leu Gly Ser His Gln
        355                 360                 365

Ile Glu Thr Asp Ile Ser Thr Ser Ser Gln Ser Pro Thr Thr Glu Thr
    370                 375                 380

Pro Arg Asn Ile His Ile Thr Trp Ala Arg Arg Tyr Leu Lys Val Ile
385                 390                 395                 400

Ile Gly Ile Ile Cys Val Ala Gly Ile Leu Leu Ile Val Ile Ser Ile
                405                 410                 415

Thr Cys Tyr Ile Arg Phe Arg His Met Arg Tyr Lys Pro Tyr Glu Val
                420                 425                 430

Ile Asn Pro Phe Pro Ala Val Tyr Thr Ser Ile Pro Ser Asn Asp Pro
        435                 440                 445

Asp Glu Leu Tyr Phe Glu Arg Ile Ala Ser Asn Asp Glu Glu Ser Ala
```

```
            450             455             460
Asp Asp Ser Phe Asp Glu Ser Asp Glu Glu Glu Pro Leu Asn Asn His
465                 470                 475                 480

His Ile Ser Thr Thr Gln His Thr Asp Ile Asn Pro Glu Lys Ser Gly
                485                 490                 495

Ser Gly Tyr Ser Val Trp Phe Arg Asp Thr Glu Asp Thr Ser Pro Gln
            500                 505                 510

Pro Leu His Ala Pro Pro Asp Tyr Ser Arg Val Val Lys Arg Leu Lys
        515                 520                 525

Ser Ile Leu Lys
    530

(2) INFORMATION FOR SEQ ID NO:4:

(i) SEQUENCE CHARACTERISTICS:
        (A) LENGTH: 100 amino acids
        (B) TYPE: amino acid
        (D) TOPOLOGY: linear (ii) MOLECULE TYPE: protein (ix) FEATURE:
        (D) OTHER INFORMATION: /label= ORF-3

(xi) SEQUENCE DESCRIPTION: SEQ ID NO:4:

Met Thr Arg Arg Val Leu Ala Pro Arg Glu Leu Glu Ala Ala Arg
 1               5                  10                  15

Lys Leu Arg Glu Ile Phe Asn Ala Glu Tyr Val Ala Pro Thr Phe Thr
                20                  25                  30

Leu Val Asp Pro Gly Asp Thr Ser Asn Ala Tyr Ile Val Cys Arg Thr
            35                  40                  45

Pro Val Thr Glu Val Val Ser Ser Ile Ser Arg Gly Ile Asp Asn Arg
        50                  55                  60

Lys Ser Val Asp Ser Ser Phe Ile Arg Ile Val Ser Lys Leu Ile Ile
65                  70                  75                  80

Arg Asn Ala Ile His Met Gly Leu Ser Val Leu Cys Ala Phe Ile Ser
                85                  90                  95

Tyr Asn Lys Pro
            100

(2) INFORMATION FOR SEQ ID NO:5:

(i) SEQUENCE CHARACTERISTICS:
        (A) LENGTH: 152 amino acids
        (B) TYPE: amino acid
        (D) TOPOLOGY: linear (ii) MOLECULE TYPE: protein (ix) FEATURE:
        (D) OTHER INFORMATION: /label= ORF-4

(xi) SEQUENCE DESCRIPTION: SEQ ID NO:5:

Met Asp His Gln Thr Ser Leu Ile Asn Ala Thr Asp Asp Asn Cys Leu
 1               5                  10                  15

Asp Thr Asp Ser Ser Ile Asn Leu Pro Ser Ile Asp Lys Cys Glu Ile
                20                  25                  30

Asp Asp Asn Ser Ile Ala Asp Glu Thr Leu Ser Asp Lys Gly Ser Pro
            35                  40                  45

Val Ala Ile Pro Leu Cys Ala Thr Ile Glu Ile Pro Arg Gly Asn Ala
        50                  55                  60
```

```
Asp Arg Gln Ser Pro Ser His Asp Val Arg Gly Ala Asn Arg Thr Asn
 65                  70                  75                  80

Tyr Asp Ser Asp Thr Gly Cys Tyr Tyr Ser Glu Ser Asp Asn Glu Thr
                 85                  90                  95

Ala Thr Leu Phe Ile Asn Arg Ile Gly Lys Arg Glu Thr Ala Lys Arg
            100                 105                 110

Arg Arg Arg Arg Cys Leu Val Ala Leu Ala Val Ser Gly Val Ala
        115                 120                 125

Thr Leu Cys Val Leu Ser Gly Leu Leu Gly Ala Leu Leu Trp Arg Leu
    130                 135                 140

Met Asp Ala Pro Gly Thr Arg Arg
145                 150
```

(2) INFORMATION FOR SEQ ID NO:6:

(i) SEQUENCE CHARACTERISTICS:
        (A) LENGTH: 213 amino acids
        (B) TYPE: amino acid
        (D) TOPOLOGY: linear (ii) MOLECULE TYPE: protein (ix) FEATURE:
        (D) OTHER INFORMATION: /label= ORF-5

(xi) SEQUENCE DESCRIPTION: SEQ ID NO:6:

```
Met Asn Arg Arg Trp Glu Asp Thr Asn Ile Glu Ser Phe Asn Met Thr
  1               5                  10                  15

Gly Val Ala Glu Met Glu Met Tyr Pro Leu Arg Gly Asp Ser Ala Asp
             20                  25                  30

His Ala Glu Thr Leu Pro Arg Ser Val Arg Ala Leu Phe Asp Ala Leu
         35                  40                  45

Arg Val Ala Ser Cys Glu Ala Phe Cys Leu Met Arg Leu Gly Gly Pro
     50                  55                  60

Pro Pro Ala Asp Ile Trp Pro Gly Val Tyr Arg Gln Tyr Arg Glu Val
 65                  70                  75                  80

Phe Arg Ser Tyr Ser Arg Ser Met Glu Gly Ser Gly Ser Pro Phe
                 85                  90                  95

His Val Ala Asp Pro Ile Arg His Leu Val Gly Arg Tyr Leu Met Gly
            100                 105                 110

Leu Gly Pro Ala Lys Pro Glu Ser His Pro Glu Leu His Thr Arg Leu
        115                 120                 125

Leu Tyr Cys Ala Tyr Trp Cys Cys Leu Gly His Ala Ala Thr Cys Thr
    130                 135                 140

His Ser His Ile Tyr Glu Asp Ala Cys Arg Arg Phe Phe Glu Glu Gly
145                 150                 155                 160

Phe Gly Ala Gly Glu Ile Pro Pro Ala Asp Ala Val Ala His Trp Asn
                165                 170                 175

Ala Leu Tyr Glu Met Val Leu Asp Glu Pro Glu Leu Leu Val Lys His
            180                 185                 190

Ala Ala Ala Val Tyr Leu Gln Arg Arg Asn Tyr Gly Gly Cys Ile
        195                 200                 205

Pro Asn Ile Glu Lys
    210
```

(2) INFORMATION FOR SEQ ID NO:7:

```
    (i) SEQUENCE CHARACTERISTICS:
        (A) LENGTH: 334 amino acids
        (B) TYPE: amino acid
        (D) TOPOLOGY: linear (ii) MOLECULE TYPE: protein (ix) FEATURE:
        (D) OTHER INFORMATION: /label= ORF-6

(xi) SEQUENCE DESCRIPTION: SEQ ID NO:7:

Met Ala Lys Gly Arg Lys His Arg Gly Arg Pro His Thr Thr Pro Ala
 1               5                  10                  15

Ala Val Lys Pro Pro Glu Leu Arg Ser Gly Arg Leu Gly His Gly Gln
                20                  25                  30

Pro Cys Gly Leu Cys Asp Gly Ser Cys Arg Leu Arg Pro Arg Gly Gly
            35                  40                  45

Leu Asn Ile Asp Pro Ser Pro Ile Leu Pro Ser Leu Thr Pro Ser Thr
        50                  55                  60

Gly Ser Ser Thr Phe Ala Ser Gln Thr Pro Gly Gly Ser Lys Ile Pro
 65                  70                  75                  80

Val Ser Cys Val Glu Thr Asp Asp Thr Ser Pro Val Arg Ala Pro Ala
                85                  90                  95

Thr Leu Pro Asp Gly Asp Asp His Pro Glu Tyr Gly Ser Val Val Ala
               100                 105                 110

Ser Arg Asp Leu Arg Ala Tyr Leu Thr His Gly Pro Gly Ala Phe Cys
               115                 120                 125

Ser Pro Pro Trp Arg Cys Asp Leu Lys Arg Leu Met Lys Asp Val Asn
130                 135                 140

Ile Met Phe Arg Cys Ile Ala Thr Ser Ser Val Asn Val Ser Ser Asp
145                 150                 155                 160

Ser Arg Ala Leu Arg Arg Ala Leu Leu Asp Phe Tyr Ile Met Gly Tyr
               165                 170                 175

Thr Asn Gln Arg Pro Thr Arg Ala Cys Trp Glu Thr Leu Leu Gln Leu
               180                 185                 190

Ser Ser Glu Gln Ala Arg Pro Leu Arg Ala Thr Leu Arg His Leu Asn
               195                 200                 205

Thr Thr Glu Pro Cys Asp Arg Arg Phe Leu Glu Pro Pro Thr Gln Val
210                 215                 220

Pro Pro Ile Leu Phe Gly Gln Glu Cys Asp Val Ser Gly Ser Glu Asp
225                 230                 235                 240

Ser Glu Asp Gly Glu Gly Val Asp Ile Glu Ser Ser Asp Ser Asp Cys
               245                 250                 255

Gly Glu Thr Ser Leu Ser Glu Phe Ser Tyr Val Gly Gly Asp Gly Asp
               260                 265                 270

Glu Thr Ser Thr Ser Asp Ser Ser Gly Thr Asp Asp Ser Asp
               275                 280                 285

Glu Thr Glu Asp Arg Ser Ser Ser Ser Glu Ser Asp Ser Ser Asp
               290                 295                 300

Val Asp Tyr Gly Thr Arg Val Cys Gly Lys Lys Arg Arg Cys Asn Pro
305                 310                 315                 320

Val Arg Arg Ser Ala Arg His Ala Ala Lys Arg Lys Met
               325                 330
```